United States Patent [19]

Abu-Nasrieh

[11] Patent Number: 5,574,154
[45] Date of Patent: Nov. 12, 1996

[54] PROCESS FOR THE PREPARATION OF CEPHALOSPORANIC COMPOUNDS

[75] Inventor: Omar Abu-Nasrieh, Amman, Jordan

[73] Assignee: Alnejma Bulk Pharmaceutical Co. A.B.P.C., Amman, Jordan

[21] Appl. No.: 315,329

[22] Filed: Sep. 29, 1994

[51] Int. Cl.$^6$ ................................................. C07D 501/06
[52] U.S. Cl. ............................ 540/222; 540/225; 540/227
[58] Field of Search ...................... 540/225, 222

[56] References Cited

U.S. PATENT DOCUMENTS

| | | |
|---|---|---|
| Re. 31,730 | 11/1984 | Bouzard et al. . |
| 4,007,174 | 2/1977 | Laundon . |
| 4,008,246 | 2/1977 | Ochiai et al. . |
| 4,033,950 | 7/1977 | Cook et al. . |
| 4,098,888 | 7/1978 | Ochiai et al. . |
| 4,152,432 | 5/1979 | Heymes et al. . |
| 4,160,863 | 7/1979 | Bouzard et al. . |
| 4,224,371 | 9/1980 | Amiard et al. . |
| 4,234,721 | 11/1980 | Bouzard et al. . |
| 4,504,657 | 3/1985 | Bouzard et al. . |
| 5,159,070 | 10/1992 | Heymes et al. . |
| 5,182,383 | 1/1993 | Osage et al. ............................ 540/223 |
| 5,359,057 | 10/1994 | Furlenmeier et al. .................. 540/222 |

Primary Examiner—Mukund J. Shah
Assistant Examiner—King Lit Wong
Attorney, Agent, or Firm—Lowe, Price, LeBlanc & Becker

[57] ABSTRACT

The invention relates to a process for the preparation of a compound of the formula I or salts thereof

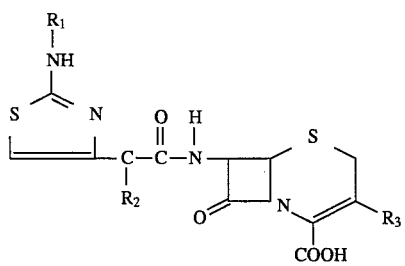

wherein
$R_1$ is hydrogen or trityl,
$R_2$ is hydrogen, trityl, $=NOCH_3$, $=NOCH_2COOH$, or $=NOCCOOH(CH_3)_2$
$R_3$ is hydrogen, $-CH=CH_2$, $-CH_2COCH_3$,

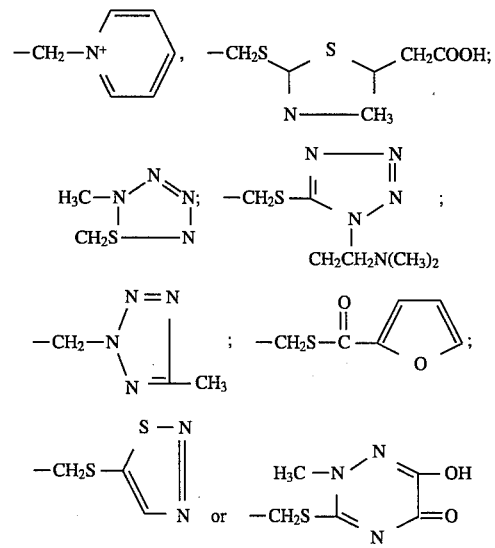

comprising (a) reacting a compound of the formula II

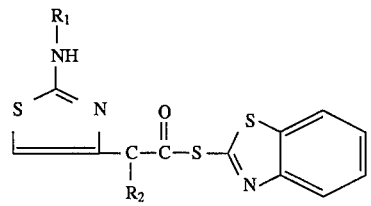

wherein $R_1$ and $R_2$ are as defined above with a compound of the formula III

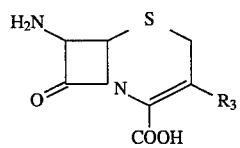

wherein $R_3$ is as defined above in the presence of a solvent; (b) refluxing the mixture in the presence of a base; and, (c) if required the compounds of the formula I so obtained are converted into salts thereof. The compounds of the formula I have antibacterial activity.

10 Claims, 1 Drawing Sheet

PROCESS FOR THE PREPARATION OF CEPHALOSPORANIC COMPOUNDS

FIELD OF THE INVENTION

The present invention relates to a process for the preparation of cephalosporanic compounds, pharmaceutical compositions containing the compounds, and methods of using the pharmaceutical compositions.

BACKGROUND OF THE INVENTION

Cephalosporin antibiotics inhibit bacteria by interfering with the synthesis of essential structural components of the bacterial cell wall. They are considered as highly effective antibiotics with low toxicity and are used for treating a wide variety of bacterial infections.

Cephalosporin C was isolated in 1952 from a mold of the genus Cephalosporium. A decade later the nucleus (7-aminocephalosporanic acid) was isolated and used as the basis for a series of synthetic derivatives, including cephalothin, cephaloridine and cephaloglycin.

Research has provided many cephalosporin derivatives with increased potency and improved stability. For example, derivatives containing a 7-aminothiazolyl group such as cefotiam have been shown to have increased potency. Resistance to β-lactamase has been found to be conferred by a methoximino group at the alpha carbon atom in the 7-acyl group. Several cephalosporins have been developed that have combined these structural features to provide highly potent enzyme resistant compounds; e.g. cefotaxime, cefmenoxime, ceftizoxime, and ceftriaxon.

Ochiai et al. (U.S. Pat. No. 4,098,888 granted Jul. 4, 1978) describe cephem compounds and processes for their preparation. Heymes et al. (U.S. Pat. No. 4,152,432) describe 3-acetoxymethyl-7-(iminoacetamido) cephalosporanic acid derivatives, in particular cefotaxime, and processes for preparing the derivatives.

SUMMARY OF THE INVENTION

The present inventor has found that cephalosporanic compounds having high potency can be prepared conveniently and in high yield by the reaction of an active ester and a 7-aminocephalosporanic acid derivative under reflux conditions. The process of the invention has many advantages over hitherto known processes. The process is essentially a one step reaction; it utilizes reflux conditions thus minimizing decomposition of the product; conversion from the (Z)-isomer to the (E)-isomer is reduced by maintaining the temperature below 45° C.; the reaction is rapid; it produces a significantly higher product yield than hitherto reported methods; and, the product of the process has a very high potency and stability.

The present invention therefore provides a process for the preparation of a compound of the formula I or salts thereof

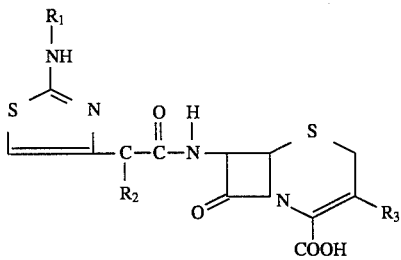

wherein
$R_1$ is hydrogen or trityl,
$R_2$ is hydrogen, trityl, $=NOCH_3$, $=NOCH_2COOH$, or $=NOCCOOH(CH_3)_2$
$R_3$ is hydrogen, $-CH=CH_2$, $-CH_2COCH_3$,

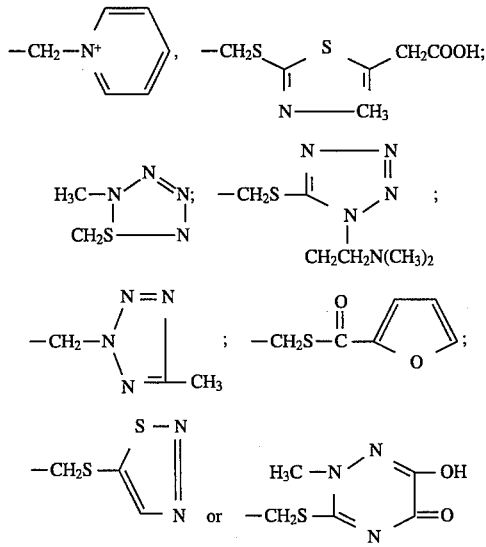

comprising (a) reacting a compound of the formula II

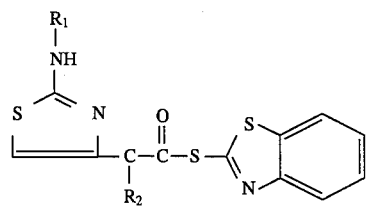

wherein $R_1$ and $R_2$ are as defined above with a compound of the formula III

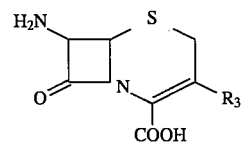

wherein $R_3$ is as defined above in the presence of a solvent; (b) refluxing the mixture in the presence of a base; and, (c) if required the compounds of the formula I so obtained are converted into salts thereof.

The invention also relates to a compound of the formula I or a salt thereof prepared by the process of the invention and a pharmaceutical composition containing at least one such compound. The invention also contemplates a method of treating bacterial infections in animals preferably humans, comprising administering to the animals an antibacterially effective amount of at least one compound or salt thereof prepared in accordance with the process of the invention.

These and other aspects of the present invention will become evident upon reference to the following detailed description and attached drawings. In addition, reference is made herein to various publications, which are hereby incorporated by reference in their entirety.

DESCRIPTION OF THE DRAWINGS

The invention will now be described in relation to the drawing in which.

DETAILED DESCRIPTION OF THE INVENTION

Figure 1:
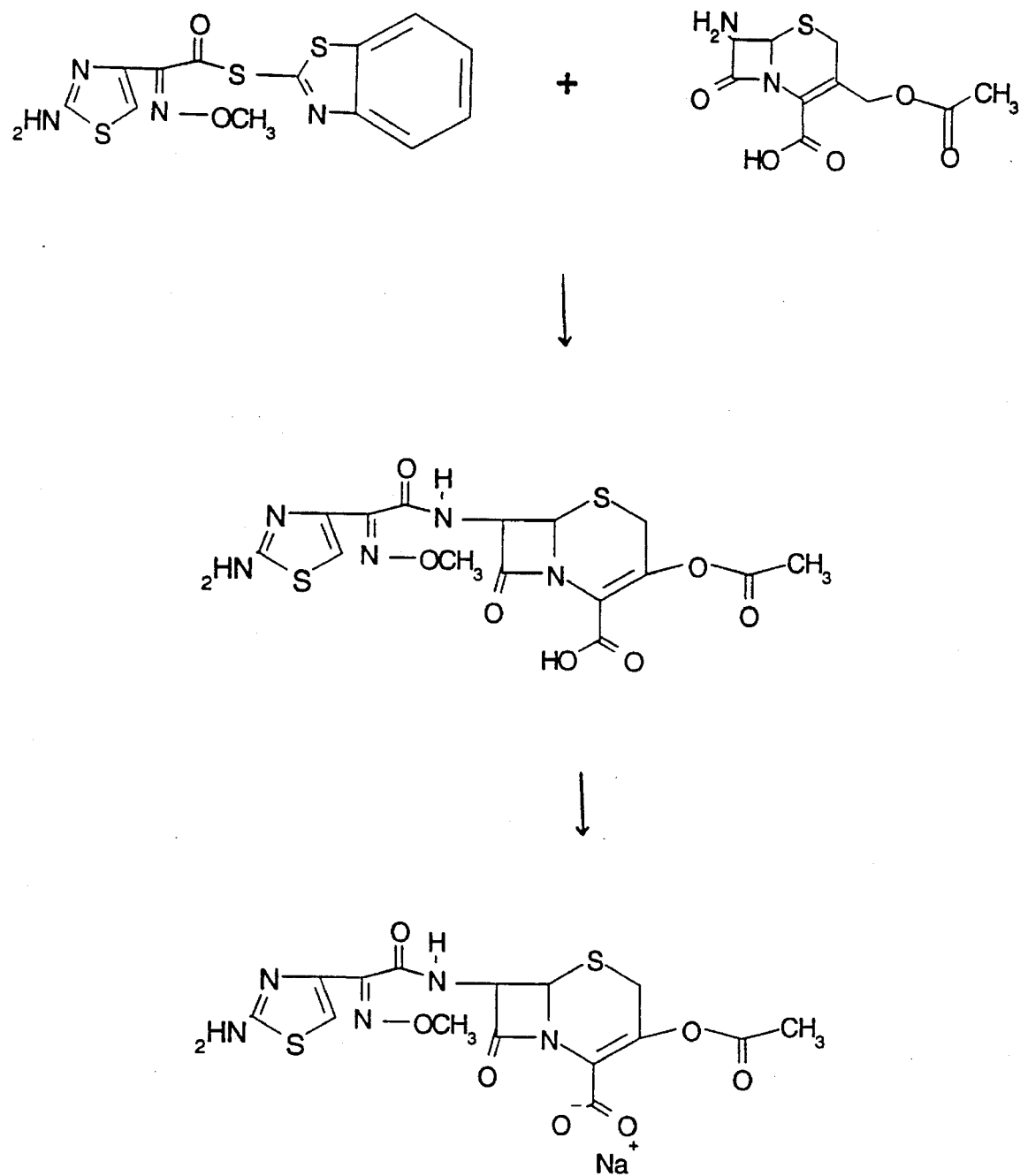
FIG. 1 is a schematic diagram showing the process of the invention.

As mentioned hereinbefore, the present invention provides a process for the preparation of cephalosporanic compounds of the formula I comprising reacting a compound of the formula II with a compound of the formula III in the presence of a solvent; refluxing the mixture in the presence of a base; and, if required the compounds of the formula I so obtained are converted into salts thereof.

In the compounds of the formula II and III used in a preferred process of the invention, $R_1$ is hydrogen, $R_2$ is $=NOCH_3$, and $R_3$ is hydrogen, $-CH_2COCH_3$,

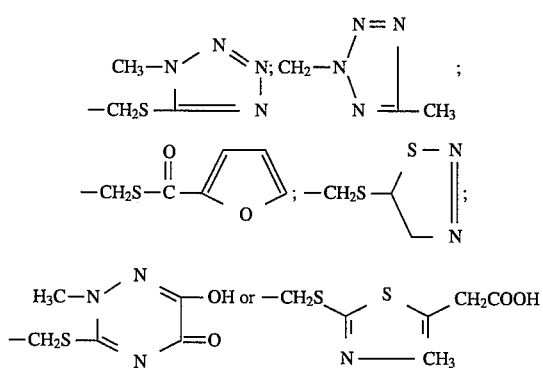

It will be appreciated that the radicals $R_1$, $R_2$ and $R_3$ may carry one or more identical or different substituents. Examples of suitable substituents include linear or branched alkyl, halogen, alkoxy, and hydroxy.

The compounds of the formula I and II are refluxed in the presence of a solvent and a base and a compound of the formula I is recovered as a condensate. Suitable solvents are acetone, acetonitrile, carbon tetrachloride, methylene chloride, toluene, methanol, ethanol, iso-propanol, dioxane, iso-propyl ether, N-methyl-pyrrolidone, and dimethylformamide. The reaction is preferably effected in methylene chloride. The base which may be used in the reaction of the compounds of the formula I and II is an trialkylamine such as triethylamine, an alkali metal carbonate, or a tertiary organic amine, preferably triethylamine. The reflux reaction is carried out at temperatures in the range from 30° C. to 45° C., and the reaction times are between 2 and 6 hours. Typically the mixture forms a gel after 1 hour. The reaction is generally carried out under nitogen blanket at atmospheric pressure.

The compounds of the formulae II and III used as starting materials in the process according to the invention are known from the literature, they can be prepared by methods known from the literature, or they can be obtained from commercial sources (Farmachen, Switzerland; Lonza, Switzerland; Biochemie, Austria, and Lupin, India).

For the process of the invention, the ratio of the amount of a compound of the formula II which is added to a compound of the formula III is about 1 to 2, preferably 1.4 to 1.6. For example, in the preparation of a compound of the formula I, 210 Kg of the compound of the formula II is reacted with 150 Kg of the compound of the formula III.

If necessary, the products of the process may be treated with a solvent such as ethanol, and purified by filtration. The filtrate is treated with an acidic agent to adjust the pH and at about pH 2.5–3 a fine powder precipitates. The powder is filtered, washed and vacuum dried to provide a compound of the formula I.

The compounds of the formula I may be converted into their corresponding salts by known methods such as by reacting with a mineral base for example sodium hydroxide, potassium hydroxide or sodium bicarbonate or by reacting with a salt of a substituted or non-substituted aliphatic carboxylic acid such as diethylacetic acid, ethylhexanoic acid or acetic acid. The preferred salts are sodium salts. Preferably, the compounds of the formula I are converted into their salts by reaction with a stoichiometric amount of sodium acetate in the presence of a solvent such as methanol, water, ethanol, or acetone. The conversion to the corresponding salts is generally carried out in the temperature range 10° C. to 25° C. and the reaction times are between about 30 minutes to 1 hour, preferably 30 minutes.

Specific examples of the compounds of the formula I which may be prepared in accordance with the process of the present invention are set forth in Table 1. In a preferred embodiment of the invention a compound of the formula I wherein $R_1$ is hydrogen, $R_2$ is $=NOCH_3$ and $R_3$ is $-CH_2OCOCH_3$ is prepared. It is also contemplated that the general process steps of the method of the invention may be used to prepare cefuroxime (The Merck Index, Eleventh Edition, Merck & Co. Inc. N.J. USA, 1989, No. 1951) and cefazolin (The Merck Index, supra, No. 1925).

The pharmacological activity of the compounds prepared by the process of the invention may be tested by employing standard in vitro and in vivo testing systems. As an example of an in vitro system, increasing doses of a compound obtained by the process of the invention may be placed in a series of tubes containing sterile nutritive media. Each tube is then seeded with a bacterial strain such as *Staphylococcus aureus, Proteus mirabilis, Bacillus subtilus, Escherichia coli*, or *Klebsiella pneumoniae* and incubated for 24 to 48 hours at 37° C. Inhibition of bacterial growth is determined by transillumination to determine the minimum inhibiting concentration (MIC in μg/ml). As an example of an in vivo system, the activity of a product obtained using the process of the invention can be studied in an animal model. For example, mice may be infected with a pathogenic bacterial strain such as *Proteus mirabilis*, and the compound can be administered subcutaneously or orally at various time intervals after the infection. The number of survivors can be determined after an appropriate length of time. The animals may also be monitored for symptoms of intoxication.

The cephalosporanic compounds prepared in accordance with the processes of the invention have a number of physiochemical and biological properties which make them very useful cephalosporin antibiotics. In particular compounds of the formula I wherein $R_1$ is hydrogen, $R_2$ is $=NOCH_3$ and $R_3$ is $-CH_2OCOCH_3$ prepared by the process of the invention are highly stable compounds with high potency as demonstrated in generally accepted test systems as described herein. The compounds are therefore very suitable for the treatment of bacterial infections, particularly infections caused by gram positive bacteria such as Staphylococcus, Streptococcus, and gram negative bacteria such as coliform bacteria, Klebsiella, Salmonella and Proteus.

Therefore, the invention also relates to a pharmaceutical composition comprising at least one compound prepared in accordance with the process of the invention. The pharmaceutical compositions of the invention contain at least one compound prepared in accordance with the processes of the invention, alone or together with other active substances.

Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets.

The pharmaceutical composition of the invention can be intended for administration to animals preferably humans. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, a compound prepared in accordance with the processes of the invention in association with one or more pharmaceutically acceptable vehicles or diluents, and contained in buffered solutions with a suitable pH and iso-osmotic with the physiological fluids.

The invention also relates to methods for treating bacterial infections in animals preferably humans, comprising administering to the animals an antibacterially effective amount of at least one compound prepared in accordance with the process of the invention. The compounds may be administered orally, rectally, parenterally or locally as described herein. Generally the dosage is between 5 to 80 mg/kg of body weight but as hereinbefore mentioned will depend on individual needs, on the desired effect and on the chosen route of administration.

The following examples are further provided for illustrative purposes only and are in no way intended to limit the scope of the present invention.

EXAMPLE 1

Preparation of Cefotaxime Acid 100 grams of 7-aminocephalosporanic acid (0.367 mol) (Joungil Corporation, South Korea) and 140 grams of 2 mercaptobenzothiazolyl (Z)-(2-aminothia 2 ol-4-yl)-methoxy iminoacetate (0.399 mol) (Farmachem, Switzerland) were suspended in 1300 ml of dichloromethane and stirred at room temperature for 5 to 10 min. 110 grams of triethylamine (0.089 mol) was added to the stirred suspension. When a clear solution was obtained, the mixture was brought to reflux for 2 to 6 hours at 40° C. The mixture formed into a gel and 250 ml of ethanol (95%) was added and the mixture was stirred for 10 minutes. The mixture was cooled to room temperature and filtered (Millipore Hazardous Filtration System, YT30142HN) to remove impurities. The pH of the filtrate was adjusted to pH 2.5 by adding 50 ml of C•HCl with stirring and a fine powder started to precipitate at pH 3–2.5. The suspension was stirred for one hour at room temperature and left to stand for 2 hours at 10°–12° C. The powder was filtered, washed with 60 ml of ethanol, and dried under vacuum to yield 105 grams of cefotaxime acid. The activity of the compound is tested using an assay of Fluka Biochemical, USA, (No. 315984-1-892, Catalogue No. 22128). ANALYSIS: Yield: 99.4%; Assay: 99.97%); Colour: White; and Solubility: very soluble in acetone and slightly soluble in water.

EXAMPLE 2

The process set out in Example 1 was carried out with varying concentrations of 7-aminocephalosporanic acid. Table 2 shows the yields and the results of an assay for activity for reactions with the various concentrations of 7-aminocephalosporanic acid.

EXAMPLE 3

Preparation of Cefotaxime Sodium

Cefotaxime Acid (200 grams) prepared according to the process described in Example 1 was placed in a round bottom flask and filtered ethanol (300 ml) was added. 1N sodium acetate in methanol solution prefiltered (100 ml) was added to the mixture while stirring to obtain a complete dissolution. The resultant mixture was filtered through a filter (Millipore Hazardous Filtration System, YT30142HN) and 800 ml of 1N sodium acetate in methanol solution prefiltered was added to the filtrate while stirring at room temperature. White crystals began to precipitate after 30 minutes from the loading of the sodium acetate solution. The suspension was stirred for an additional one hour. The white powder was filtered and washed with 50 ml of filtered acetone. The powder was dried under vacuum to yield 190 grams of cefotaxime sodium sterile. ANALYSIS: Yield: 91%; Assay: 99.42%; Colour: very white (compared to commercial yellow product); and Solubility: very soluble in water.

While what is shown and described herein constitutes various preferred embodiments of the device and method subject invention, it will be understood that various changes can be made to such embodiments without departing from the subject invention, the scope of which is defined in the appended claims.

TABLE 1

| Compound | $R_1$ | $R_2$ | $R_3$ |
|---|---|---|---|
| Cefotaxime | H | $=NOCH_3$ | $-CH_2OCOCH_3$ |
| Cefixime | H | $=NOCH_2COOH$ | $-CH=CH_2$ |
| Cefmenoxime | H | $=NOCH_3$ | $H_3C-N\overset{N}{\underset{CH_2S}{\diagdown}}\overset{}{\diagup}N$ |
| Cefodizime | H | $=NOCH_3$ | $-CH_2S\diagdown S\diagup CH_2COOH$, $N-CH_3$ |

TABLE 1-continued

| Compound | R₁ | R₂ | R₃ |
|---|---|---|---|
| Ceftibuten | H | =C—CH₂COOH (with H below) | H |
| Ceftiofur | H | =NOCH₃ | —CH₂S—C(=O)—(furan) |
| Ceftizoxime | H | =NOCH₃ | H |
| Ceftriaxone | H | =NOCH₃ | —CH₂S—(triazine with H₃C—N, N, OH, =O) |
| Cefuzonam | H | =NOCH₃ | —CH₂S—(thiadiazole) |
| Cefotiam | H | H | —CH₂S—(tetrazole)—CH₂CH₂N(CH₃)₂ |
| Ceftazidime | H | —N—OC(CH₃)₂ / COOH | —CH₂—N⁺(pyridine) |
| Cefteram | H | =NOCH₃ | —CH₂—N(tetrazole)—CH₃ |

TABLE 2

| Exp. No. | 7-ACA Used (g) | Yield (%) | Assay (%) |
|---|---|---|---|
| 1 | 50 | 97.5 | 99.57 |
| 2 | 50 | 98.7 | 99.73 |
| 3 | 60 | 98.4 | 99.70 |
| 4 | 100 | 99.4 | 99.8 |
| 5 | 200 | 99.4 | 99.99 |

I claim:

1. A process for the preparation of a compound of formula I or salts thereof

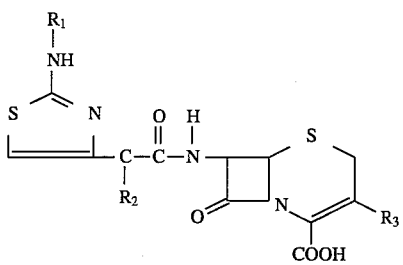

wherein R₁ is hydrogen or trityl, R₂ is =NOCH₃, R₃ is hydrogen, —CH₂COCH₃,

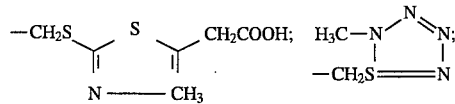

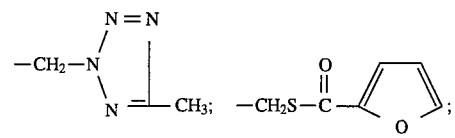

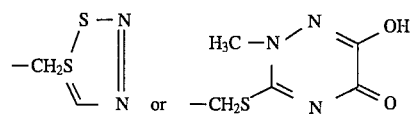

comprising (a) mixing a compound of the formula II

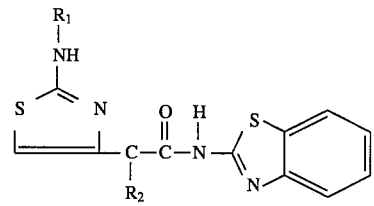

wherein R₁ and R₂ are as defined above with a compound of the formula III

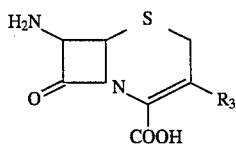

wherein $R_3$ is as defined above in the presence of a solvent; (b) refluxing the resulting mixture at about 30°–45° C. in the presence of a base selected from the group consisting of an alkali metal carbonate and a tertiary organic amine to produce a condensate; (c) precipitating a compound of the formula I from the condensate; and, (d) if required, converting the compounds of formula I so obtained into salts thereof.

2. The process as claimed in claim 1 wherein in the compound of Formula I, $R_1$ is hydrogen, $R_2$ is =$NOCH_3$, and $R_3$ is —$CH_2COCH_3$.

3. The process as claimed in claim 1 wherein in step (c) a compound of formula I is precipitated without using phase separation, by adjusting the pH to between about 2.5 and 3.5.

4. The process as claimed in claim 1 wherein the compounds of formula I are converted into sodium salts.

5. The process as claimed in claim 1 wherein the base is a trialkylamine.

6. The process as claimed in claim 1 wherein the solvent is selected from the group of solvents consisting of acetone, acetonitrile, carbon tetrachloride, methylene chloride, toluene, dioxane, isopropyl ether, N-methyl-pyrrolidone, methanol, ethanol, propanol, isopropanol, and dimethylformamide.

7. The process as claimed in claim 1 wherein the solvent is methylene chloride.

8. The process as claimed in claim 1 wherein the base is triethylamine.

9. The process as claimed in claim 1 wherein the base is triethylamine.

10. The process as claimed in claim 1 wherein the compounds of formula I are converted into sodium salts.

* * * * *